United States Patent [19]
Taylor

[11] Patent Number: 6,001,112
[45] Date of Patent: Dec. 14, 1999

[54] ROTATIONAL ATHERECTOMY DEVICE

[75] Inventor: Paul Taylor, Poway, Calif.

[73] Assignee: Endicor Medical, Inc., San Clemente, Calif.

[21] Appl. No.: 09/058,513

[22] Filed: Apr. 10, 1998

[51] Int. Cl.$^6$ .................................................. A61B 17/00
[52] U.S. Cl. ......................................................... 606/159
[58] Field of Search ..................................... 606/159–167, 606/170, 171, 180, 1; 604/96, 22; 128/898, 899

[56] References Cited

U.S. PATENT DOCUMENTS

| | | |
|---|---|---|
| 2,701,559 | 2/1955 | Cooper . |
| 2,850,007 | 9/1958 | Lingley . |
| 3,082,805 | 3/1963 | Royce . |
| 3,614,953 | 10/1971 | Moss . |
| 3,732,858 | 5/1973 | Banko . |
| 3,749,085 | 7/1973 | Willson et al. . |
| 3,845,375 | 10/1974 | Stiebel . |
| 3,945,375 | 3/1976 | Banko . |
| 3,976,077 | 8/1976 | Kerfoot, Jr. . |
| 4,038,985 | 8/1977 | Chiulli . |
| 4,177,797 | 12/1979 | Baylis et al. . |
| 4,273,128 | 6/1981 | Lary . |
| 4,436,091 | 3/1984 | Banko . |
| 4,445,509 | 5/1984 | Auth . |
| 4,512,344 | 4/1985 | Barber . |
| 4,589,412 | 5/1986 | Kensey . |
| 4,631,052 | 12/1986 | Kensey . |
| 4,646,736 | 3/1987 | Auth . |
| 4,646,738 | 3/1987 | Trott . |
| 4,669,469 | 6/1987 | Gifford, III et al. . |
| 4,686,982 | 8/1987 | Nash . |
| 4,696,667 | 9/1987 | Masch . |
| 4,706,671 | 11/1987 | Weinrib . |
| 4,728,319 | 3/1988 | Masch . |
| 4,729,763 | 3/1988 | Henrie . |
| 4,732,154 | 3/1988 | Shiber . |
| 4,747,406 | 5/1988 | Nash . |
| 4,754,755 | 7/1988 | Husted . |
| 4,771,774 | 9/1988 | Simpson et al. . |
| 4,781,186 | 11/1988 | Simpson et al. . |
| 4,784,636 | 11/1988 | Rydell . |
| 4,790,812 | 12/1988 | Hawkins, Jr. et al. . |
| 4,794,931 | 1/1989 | Yock . |
| 4,819,634 | 4/1989 | Shiber . |
| 4,842,579 | 6/1989 | Shiber . |
| 4,844,064 | 7/1989 | Thimsen et al. . |
| 4,850,957 | 7/1989 | Summers . |
| 4,857,046 | 8/1989 | Stevens et al. . |
| 4,867,157 | 9/1989 | McGurk-Burleson et al. . |
| 4,883,458 | 11/1989 | Shiber . |
| 4,886,490 | 12/1989 | Shiber . |
| 4,887,613 | 12/1989 | Farr et al. . |
| 4,894,051 | 1/1990 | Shiber . |
| 4,919,133 | 4/1990 | Chiang . |

(List continued on next page.)

FOREIGN PATENT DOCUMENTS

| | | |
|---|---|---|
| 2000621 | of 0000 | Canada . |
| 0 086 048 A2 | 8/1983 | European Pat. Off. . |
| 0 291 170 A1 | 11/1988 | European Pat. Off. . |
| 0 421 457 A1 | 10/1989 | European Pat. Off. . |
| 0 373 927 A2 | 6/1990 | European Pat. Off. . |
| 0 463 798 A1 | 1/1992 | European Pat. Off. . |
| 37 322236 | 12/1988 | Germany . |
| 5-42162 | of 0000 | Japan . |
| 5-56984 | of 0000 | Japan . |
| 2-271847 | 12/1989 | Japan . |
| 442795 | 9/1974 | U.S.S.R. . |
| WO 89/06517 | 7/1989 | WIPO . |
| WO 93/13716 | 7/1993 | WIPO . |
| WO 93/13717 | 7/1993 | WIPO . |

*Primary Examiner*—Michael Buiz
*Assistant Examiner*—Vikki Trinh
*Attorney, Agent, or Firm*—Knobbe, Martens, Olson & Bear LLP

[57] ABSTRACT

An elongate tubular body extends between a rotatable cutter tip and a control. The cutter tip is connected to the control with a rotatable element. The control has an indicator which reveals resistance to rotation of either the rotatable element or cutter tip. Material which has been processed by the cutter tip is aspirated through the tubular body for disposal.

34 Claims, 6 Drawing Sheets

U.S. PATENT DOCUMENTS

| | | |
|---|---|---|
| 4,923,462 | 5/1990 | Stevens . |
| 4,926,858 | 5/1990 | Gifford, III et al. . |
| 4,957,482 | 9/1990 | Shiber . |
| 4,979,939 | 12/1990 | Shiber . |
| 4,979,951 | 12/1990 | Simpson . |
| 4,986,807 | 1/1991 | Farr . |
| 4,990,134 | 2/1991 | Auth . |
| 4,994,067 | 2/1991 | Summers . |
| 5,002,553 | 3/1991 | Shiber . |
| 5,007,896 | 4/1991 | Shiber . |
| 5,009,659 | 4/1991 | Hamlin et al. . |
| 5,019,088 | 5/1991 | Farr . |
| 5,026,384 | 6/1991 | Farr et al. . |
| 5,047,040 | 9/1991 | Simpson et al. . |
| 5,071,425 | 12/1991 | Gifford, III et al. . |
| 5,074,841 | 12/1991 | Ademovic et al. . |
| 5,078,722 | 1/1992 | Stevens . |
| 5,078,723 | 1/1992 | Stevens . |
| 5,087,265 | 2/1992 | Summers . |
| 5,092,873 | 3/1992 | Simpson et al. . |
| 5,112,345 | 5/1992 | Farr . |
| 5,114,399 | 5/1992 | Kovalcheck . |
| 5,181,920 | 1/1993 | Mueller et al. . |
| 5,192,291 | 3/1993 | Pannek, Jr. . |
| 5,195,956 | 3/1993 | Stockmeier . |
| 5,222,966 | 6/1993 | Perkins et al. . |
| 5,224,945 | 7/1993 | Pannek, Jr. . |
| 5,242,460 | 9/1993 | Klein et al. . |
| 5,263,959 | 11/1993 | Fischell . |
| 5,269,793 | 12/1993 | Simpson . |
| 5,295,493 | 3/1994 | Radisch, Jr. . |
| 5,356,418 | 10/1994 | Shturman . |
| 5,358,472 | 10/1994 | Vance et al. . |
| 5,358,485 | 10/1994 | Vance et al. . |
| 5,366,463 | 11/1994 | Ryan . |
| 5,370,609 | 12/1994 | Drasler et al. . |
| 5,370,651 | 12/1994 | Summers . |
| 5,395,311 | 3/1995 | Andrews . |
| 5,403,334 | 4/1995 | Evans et al. . |
| 5,409,454 | 4/1995 | Fischell et al. . |
| 5,423,799 | 6/1995 | Shiu . |
| 5,423,846 | 6/1995 | Fischell . |
| 5,441,510 | 8/1995 | Simpson et al. . |
| 5,507,292 | 4/1996 | Jang et al. . |
| 5,507,760 | 4/1996 | Wynne et al. . |
| 5,512,044 | 4/1996 | Duer ................................ 604/22 |
| 5,514,115 | 5/1996 | Frantzen et al. . |
| 5,556,408 | 9/1996 | Farhat . |
| 5,632,755 | 5/1997 | Nordgren et al. . |
| 5,649,941 | 7/1997 | Lary . |
| 5,669,920 | 9/1997 | Conley et al. . |
| 5,681,336 | 10/1997 | Clement et al. . |
| 5,695,506 | 12/1997 | Pike et al. . |
| 5,695,507 | 12/1997 | Auth et al. . |
| 5,697,944 | 12/1997 | Lary . |
| 5,700,240 | 12/1997 | Baarwick et al. ............... 606/159 X |
| 5,792,157 | 8/1998 | Mische et al. . |
| 5,836,957 | 11/1998 | Schulz et al. . |
| 5,843,103 | 12/1998 | Wulfman . |
| 5,873,882 | 2/1999 | Straub et al. ..................... 606/159 |

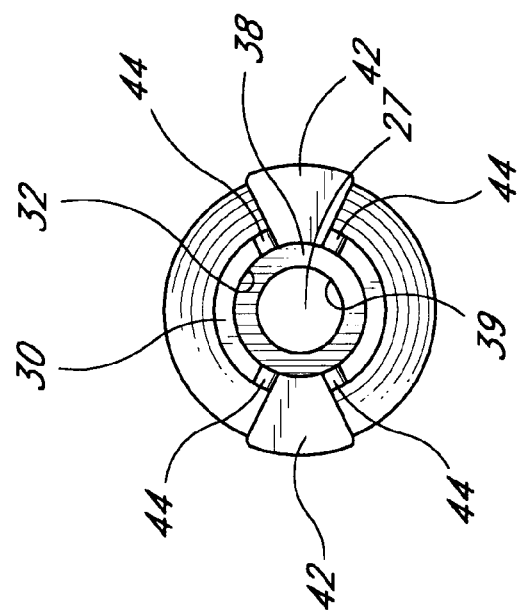
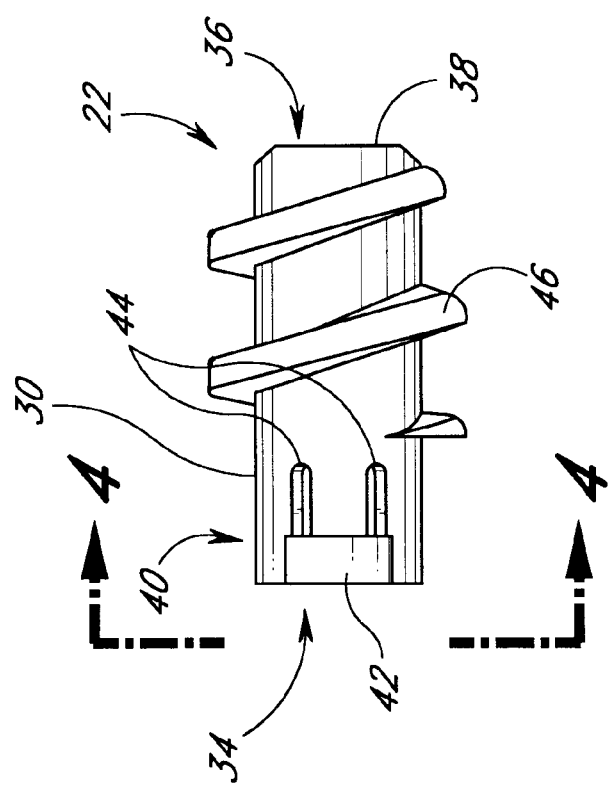

ROTATIONAL ATHERECTOMY DEVICE

BACKGROUND OF THE INVENTION

This invention relates to medical devices and particularly to a rotational atherectomy catheter device.

A variety of techniques and instruments have been developed for use in the removal or repair of obstructive material in arteries and other body passageways. A frequent objective of such techniques and instruments is the removal of atherosclerotic plaques in a patient's arteries. Atherosclerosis is characterized by the buildup of fatty deposits (atheromas) in the intimal layer (under the endothelium of a patient's blood vessels). Over time, what initially is deposited as relatively soft cholesterol-rich atheromatous material often hardens into a calcified atherosclerotic plaque. Such atheromas are often referred to as stenotic lesions or stenoses, the blocking material being referred to as stenotic material. If left untreated, such stenoses can so sufficiently reduce perfusion that angina, hypertension, myocardial infarction, strokes and the like may result.

Several kinds of atherectomy devices have been developed for attempting to remove some or all of such stenotic material. In one type of device, such as that shown in U.S. Pat. No. 5,092,873 (Simpson), a cylindrical housing, carried at the distal end of a catheter, has a portion of its side-wall cut out to form a window into which the atherosclerotic plaque can protrude when the device is positioned next to the plaque. An atherectomy blade, disposed within the housing, is then advanced the length of the housing to lance the portion of the atherosclerotic plaque that extends into the housing cavity. While such devices provide for directional control in selection of tissue to be excised, the length of the portion excised at each pass of the atherectomy blade is necessarily limited to the length of the cavity in the device. The length and relative rigidity of the housing limits the maneuverability and therefore also limits the utility of the device in narrow and tortuous arteries such as coronary arteries. Such devices are also generally limited to lateral cutting relative to the longitudinal axis of the device.

Another approach which solves some of the problems relating to removal of atherosclerotic plaque in narrow and tortuous passageways involves the use of an abrading device carried at the distal end of a flexible drive shaft. Examples of such devices are illustrated in U.S. Pat. Nos. 4,990,134 (Auth) and 5,314,438 (Shturman). In the Auth device, abrasive material such as diamond grit (diamond particles or dust) is deposited on a rotating burr carried at the distal end of a flexible drive shaft. In the Shturman device, a thin layer of abrasive particles is bonded directly to the wire turns of an enlarged diameter segment of the drive shaft. The abrading device in such systems is rotated at speeds up to 200,000 rpm or more, which, depending on the diameter of the abrading device utilized, can provide surface speeds of the abrasive particles in the range of 40 ft/sec. According to Auth, at surface speeds below 40 ft/sec his abrasive burr will remove hardened atherosclerotic materials but will not damage normal elastic soft tissue of the vessel wall. See, e.g., U.S. Pat. No. 4,990,134 at col. 3, lines 20–23.

However, not all atherosclerotic plaques are hardened, calcified atherosclerotic plaques. Moreover, the mechanical properties of soft plaques are very often quite close to the mechanical properties of the soft wall of the vessel. Thus, one cannot always rely entirely on the differential cutting properties of such abrasives to remove atherosclerotic material from an arterial wall, particularly where one is attempting to entirely remove all or almost all of the atherosclerotic material.

Moreover, a majority of atherosclerotic lesions are asymmetrical (i.e., the atherosclerotic plaque is thicker on one side of the artery than on the other). Since the stenotic material will be entirely removed on the thinner side of an eccentric lesion before it will be removed on the other, thicker side of the lesion, during removal of the remaining thicker portion of the atherosclerotic plaque the abrasive burr of the Auth device or the abrasive-coated enlarged diameter segment of the drive shaft of the Shturman device necessarily will be engaging healthy tissue on the side which has been cleared. Indeed, lateral pressure by such healthy tissue against the abrading device is required to keep the abrading device in contact with the remaining stenotic tissue on the opposite wall of the passageway. For stenotic lesions that are entirely on one side of an artery (a relatively frequent condition), this means that the healthy tissue across from the stenotic lesion will be exposed to and in contact with the abrading device for substantially the entire procedure. Moreover, pressure from that healthy tissue against the abrading device will be, in fact, the only pressure urging the abrading device against the atherosclerotic plaque. Under these conditions, a certain amount of damage to the healthy tissue is almost unavoidable, even though undesirable, and there is a clear risk of perforation or proliferative healing response. In some cases, this "healthy tissue" across from a stenotic lesion may itself be somewhat hardened (i.e., it has diminished elasticity); under such circumstances, the differential cutting phenomenon described by Auth will also be diminished, resulting in a risk that this "healthy" tissue may also be removed, potentially causing perforation.

Thus, notwithstanding the foregoing and other efforts to design a rotational atherectomy device, there remains a need for such a device which can advance through soft atheromas while providing minimal risk to the surrounding vessel wall. Preferably, the device also minimizes the risk of dislodging emboli, and provides the clinician with real-time feedback concerning the progress of the procedure.

SUMMARY OF THE INVENTION

In accordance with one aspect of the present invention, a rotational medical device is provided having an elongate flexible tubular body. The tubular body has a proximal end and a distal end. The tubular body also has a rotatable element which extends throughout its length. At the distal end of the tubular body is a rotatable cutter tip which is connected to the rotatable element. At the proximal end of the tubular body is a control having an indicator which indicates the resistance to rotation of either the cutter tip or the rotatable element. Preferably, the tubular body is provided with a vacuum coupling to permit aspiration of material dislodged by the cutter tip.

In accordance with another aspect of the present invention, a method of removing material from a vessel is provided. The first step of the method is providing an elongate flexible tubular body having a proximal end with a control and a distal end with a rotatable cutter tip. The distal end of the elongate body is then advanced transluminally through the vessel to the material to be removed. The rotatable cutter tip is then rotated. Next, portions of the material to be removed are drawn by application of a vacuum proximally past the rotatable cutter tip and into the tubular body. Feedback may be provided to the operator in response to changes in the load on the rotatable cutter tip.

In accordance with a further aspect of the present invention, a rotatable tip for use in an elongate flexible tubular catheter is provided for removing material from a vessel. The tip has a tip body having a proximal end and a distal end and a longitudinal axis of rotation extending between the two ends. A generally helical thread is provided on at least a distal portion of the tip body. Also, at least one radially outwardly extending cutter is provided on a proximal portion of the tip body.

A rotational medical device having an elongate flexible tubular body is provided in accordance with another aspect of the present invention. The tubular body has a proximal end and a distal end. A rotatable element is contained within and projecting distally from the flexible tubular body such that the rotatable element is either in sliding contact with or is spaced radially inward from the tubular body. An aspiration lumen extends within the tubular body between the interior surface of a wall of the tubular body and the exterior surface of the rotatable element. At the distal end of the tubular body, the present invention provides a rotatable tip which is connected to the rotatable element. The present invention also provides a control at the proximal end of the tubular body. The tubular body has a first cross-sectional area and the aspiration lumen has a second cross-sectional area wherein the cross-sectional area of the aspiration lumen is at least about 30% and preferably is as much as 50% or more of the cross-sectional area of the tubular body.

Preferably, a guidewire lumen extends throughout the length of the tubular body, or through at least a distal portion of the tubular body. The catheter may be used with either a conventional closed tip guidewire, or with a hollow guidewire having a distal opening thereon such as for infusion of therapeutic drugs, contrast media or other infusable material.

In accordance with another aspect of the present invention, a method of removing material from a patient is also provided. An elongate flexible tubular body, having a proximal end and a distal end, is provided. The tubular body has a rotatable tip on the distal end and a control on the proximal end. The rotatable tip is advanced to the location of the material to be removed. The control is manipulated to activate a vacuum through the tubular body. Then the control is manipulated to commence a rotation of the rotatable tip to remove the material from the patient.

BRIEF DESCRIPTION OF THE DRAWINGS

FIG. 3 is a side elevational view of the cutter tip of FIG. 2;

FIG. 4 is an end view taken along the line 4—4 of the cutter tip of FIG. 3;

DETAILED DESCRIPTION OF PREFERRED EMBODIMENTS

Figure 1:
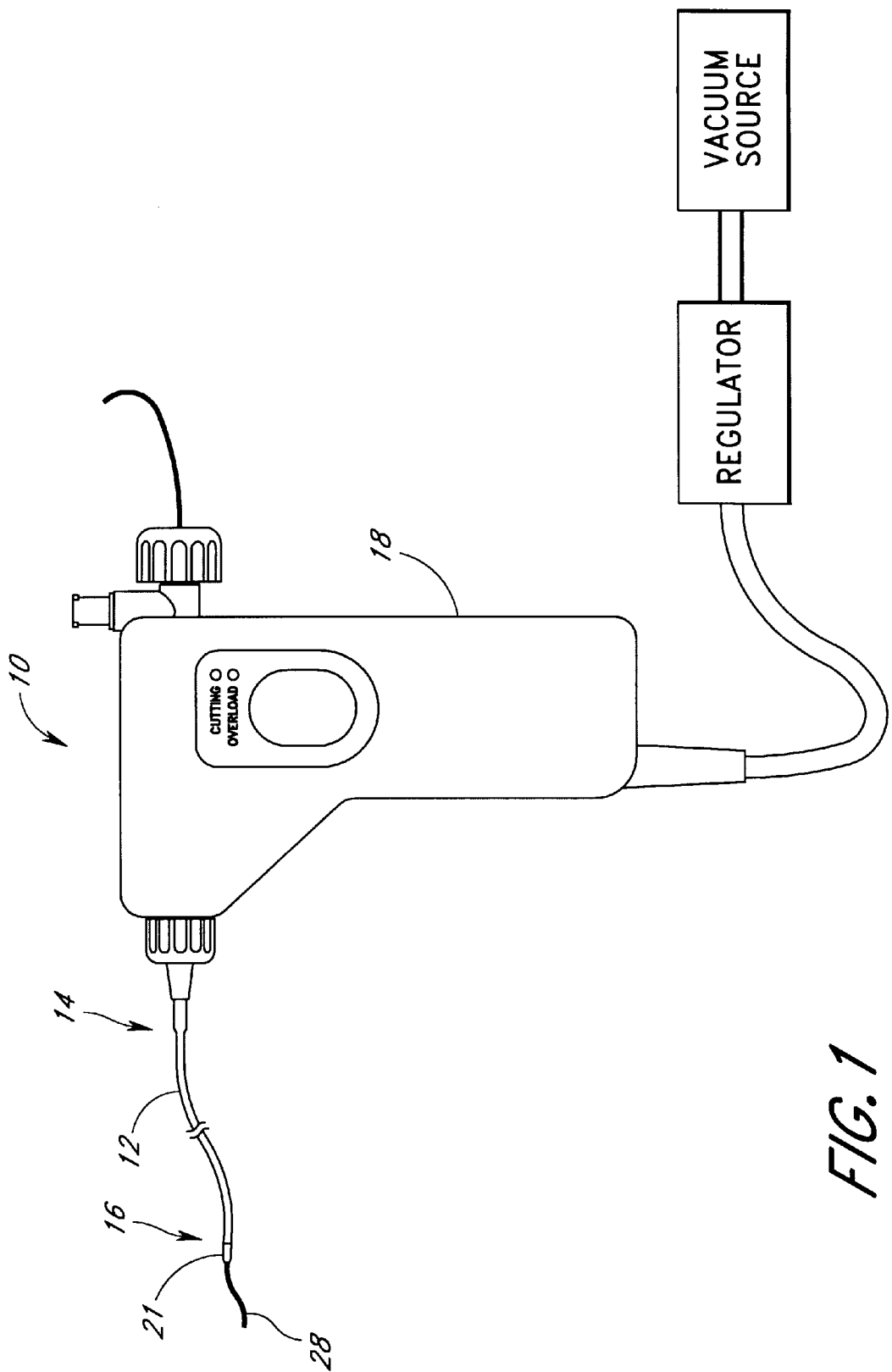
FIG. 1 is a schematic view of the device of the present invention.

Referring to FIG. 1, an illustrative embodiment of the inventive surgical instrument 10 is shown. In general, the surgical instrument 10 comprises an elongate flexible tubular body 12 having a proximal end 14 and a distal end 16. A control 18 is provided on the proximal end 14 of the tubular body 12 for permitting manipulation of the instrument 10. The control 18 carries electronic controls and indicators as well as vacuum controls as will be discussed below.

Figure 2:
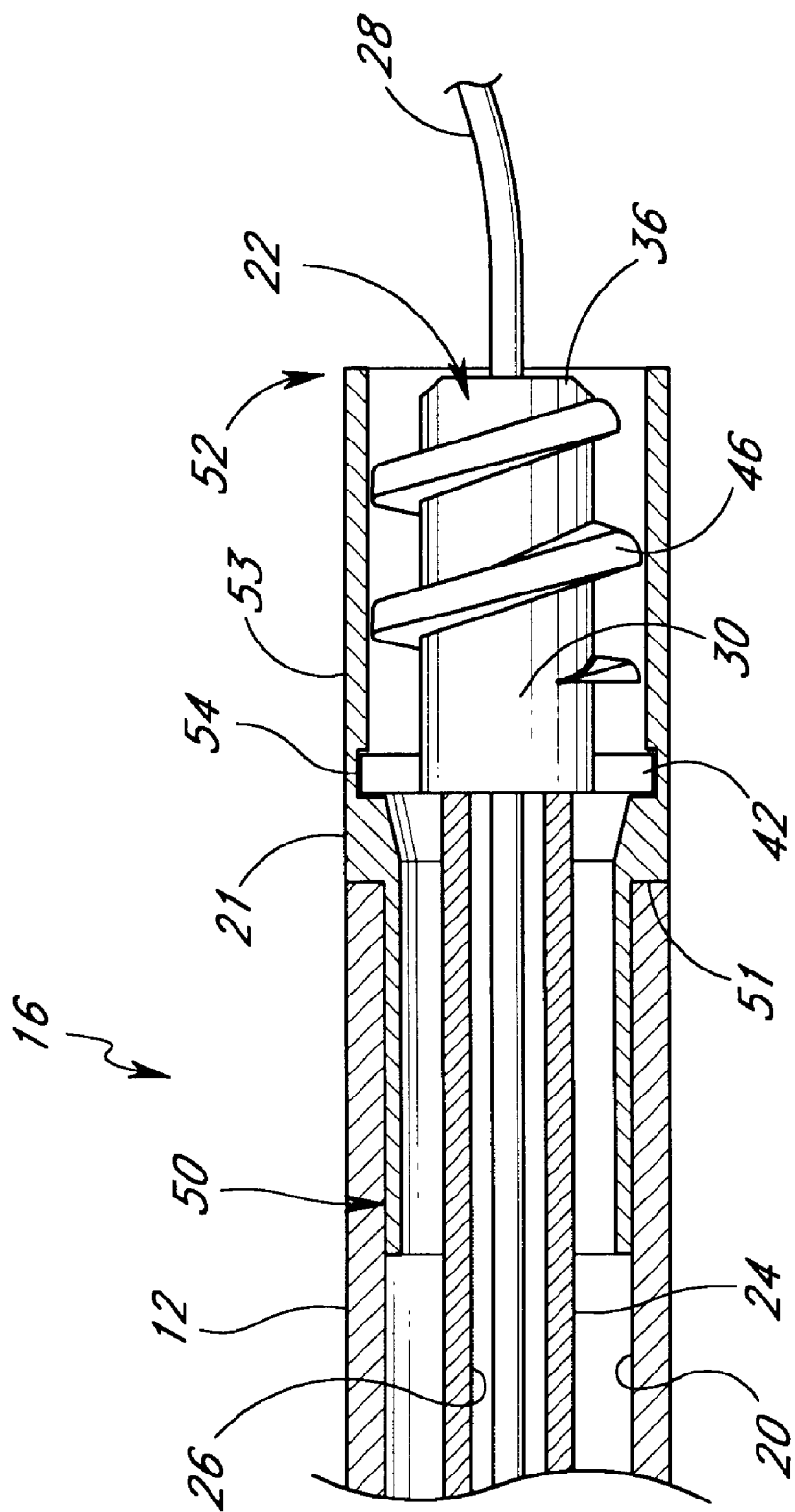
FIG. 2 is a cross-sectional side elevational view of the distal tip of the device of FIG. 1, showing an embodiment of the cutter assembly.

Referring to FIG. 2, the tubular body 12 is provided with an elongate central lumen 20 and a cutter housing 21 for rotatably receiving a cutter tip 22. Cutter tip 22 is rotationally coupled to the control 18 by way of an elongate flexible drive shaft 24. In an over-the-wire embodiment, the drive shaft 24 and cutter tip 22 are provided with an axially extending central lumen 26 for slidably receiving a guidewire 28 as will be understood by those of skill in the art.

The diameter of the guidewire 28 is generally in the range of about 0.010 inches to about 0.020 inches. The length of the guidewire 28 may be varied to correspond to the distance between the percutaneous access site and the lesion being operated upon. For example, the guidewire 28 should be long enough to allow the cutter tip 22 of the present surgical instrument 10 to track along the guidewire 28 and reach the target occlusion while also allowing a proximal portion of the guidewire to remain exterior to the patient for manipulation by the clinician. In an application for removing coronary artery atheroma by way of a femoral artery access, guidewires 28 having lengths from about 120 cm to about 160 cm may be used as will be understood by those of skill in art. For other applications, such as peripheral vascular procedures including recanalization of implanted vascular grafts, the length of the guidewire 28 will depend upon the location of the graft of other treatment site relative to the percutaneous puncture. Suitable guidewires 28 for coronary artery applications include those manufactured by Guidant or Cordis.

To accommodate the guidewire 28, as shown in FIGS. 3 and 4, one embodiment of the present cutter tip 22 includes a generally cylindrical sleeve shaped body 30 having a central lumen 32. The cylindrical body 30 of cutter tip 22 generally has an external diameter of between about 0.056 inches and 0.092 inches. In one embodiment, the external diameter is approximately 0.042 inches. The body 30 has a wall thickness between about 0.003 and about 0.010 inches. In one embodiment, the wall thickness is about 0.009 inches. The length of one embodiment of the present cutter tip 22 is approximately 0.096 inches but the length may alternatively vary from about 0.040 to about 0.120. In general, tip 22 lengths of no more than about 0.100 are preferred; shorter tip lengths permit greater lateral flexibility and enable remote access as will be apparent to those of skill in the art.

As shown in FIG. 3, the cylindrical body 30 of the present cutter tip 22 has a proximal end 34 and a distal end 36. In one embodiment, an end cap 38 is provided on the distal end 36 of the present cutter tip 22. The end cap 38 is preferably disk shaped to correspond to the cylindrical body 30 of the present cutter tip 22. The end cap 38 has a thickness of approximately 0.007 inches. However, the end cap 38 thickness may range from 0.003 to 0.020. The end cap 38 has an outside diameter which corresponds to the outside diameter of the distal end 26 of the present cutter tip 22. End cap 38 has a centrally located aperture 39. The aperture 39 preferably has a diameter of between about 0.017 and about 0.025. In one embodiment, the aperture 39 has a diameter of approximately 0.022 inches. Additionally, the outside distal edge of the end cap 38 is desirably rounded such that the sharp machined edge is removed. Alternatively, the end cap 38 may be a unitary portion of the present cutter tip 22.

A connector portion 40 is provided on the proximal end 34 of the present cutter tip 22 for rotatably interlocking the cutter tip 22 within the cutter housing 21. The connector portion 40 may take various forms as will be appreciated by one skilled in the art. In the embodiment shown in FIGS. 3 and 4, the connector 40 comprises two radially outwardly extending supports such as wedge-shaped cutter blocks 42. The cutter blocks 42 may be formed by removing material from an annular flange at the proximal end 34 of the cutter tip 22.

Although two opposing cutter blocks 42 are illustrated in FIGS. 3 and 4, three or four or more cutters may be utilized as will be apparent to those of skill in the art. In general, the cutters will be circumferentially evenly distributed about the longitudinal axis of the cutter tip, to improve balance during rotation of the tip. For example, three cutters would preferably extend radially outwardly from the cylindrical wall 30 on 120° centers. Similarly, four radially outwardly extending cutters would be located on 90° centers.

The illustrated connector 40 has an outside diameter taken through the opposing cutter blocks of approximately 0.071. The outside diameter will generally range from about 0.057 to about 0.096. The thickness of the cutter blocks taken in the axial direction is about 0.010 but may range from about 0.004 to about 0.025. In general, the OD through cutter blocks 42 is selected to cooperate with the inside diameter of an annular retaining groove 54 discussed below, to axially retain the tip 22 while permitting rotation thereof with respect to the housing 21.

As shown in FIG. 3, the cutter tip 22 also has two axially extending slots 44 which are formed in the cylindrical wall 30 adjacent each cutter block 42. The slots 44 are preferably about 0.005 inches in width; however the width may range from approximately 0.001 to approximately 0.025. The slots 44 of the present cutter tip 22 are also at least about 0.025 in length along the longitudinal axis of the body 30. One skilled in the art will readily appreciate that the slots 44 of the present cutter tip 22 can be varied in axial length to vary the radially outwardly directed force on the cutter block 42. The slots 44 allow radial inward compression of the connector 40 of the cutter tip 22 to allow for ease of assembly of the cutter tip 22 with the cutter housing 21 as described below.

As shown in FIGS. 2–4, an external helical thread 46 extends along a portion of the exterior surface of the cylindrical body 30 of the present cutter tip 22. The thread 46 preferably extends from a location on the cylindrical body 30 which is distal to the connector 40. In one embodiment having a cutter housing 21 with an inside diameter of about 0.0685, the major diameter of the thread 46 is approximately 0.0681 inches. However, the major diameter of the present thread 46 may range from about 0.050 to about 0.130 or otherwise, depending upon the intended clinical application. The helical thread 46 of the foregoing embodiment has a pitch of approximately 0.0304 inches. The pitch may range from about 0.005 to about 0.060, and may be constant or variable along the axial length of the cutter tip 22. The thickness of the present thread 46 in the axial direction is approximately 0.008 inches; however, the thickness may range from about 0.003 to about 0.05, and may be constant or variable along the length of the thread 46.

In the embodiment illustrated in FIG. 2, the outside diameter of the thread 46 has a close sliding fit with the inside diameter of the cutter housing 21. In this configuration, the atheromatous material will be cut by the helical threads and assisted by the cutter blocks 42. However, it may be desirable in some embodiments to provide an annular space between the outside diameter of the thread 46 and the inside diameter of the cutter housing 21. By spacing the thread 46 radially inwardly from the inside wall of the central lumen, an annular space is provided for material to pass through the cutter without being severed by the thread 46. This may be utilized in conjunction with the vacuum, discussed below, to aspirate material into the atherectomy device without the necessity of complete cutting by the thread 46. This may be advantageous if the aspiration rate is desirably set higher than the rate which would occur if otherwise limited by the thread 46. In addition, certain lesion morphologies, such as those including portions of calcified plaque, may be more readily aspirated by the rotational atherectomy device if the thread 46 is not required to cut all the way through the aspirated material. In general, the radial distance between the thread 46 and the inside wall of the cutter housing 21 will be within the range of from about 0.0001 to about 0.008, to be optimized in view of the desired performance characteristics of the particular embodiment. In an embodiment intended solely to aspirate soft atheromas, the thread 46 may be deleted entirely, so that cutting occurs by the cutting blocks 42 in cooperation with the aspiration provided by the vacuum source.

As shown in FIGS. 2 and 3, the illustrated thread 46 makes approximately two turns about the cylindrical body 30; however, one skilled in the art will readily appreciate that the thread 46 may make as few as about 0.25 and as many as about 10 turns about the cylindrical body 30 of the cutter tip 22. In addition, while the present cutter tip 22 is illustrated and described as having a single thread, one skilled in the art will appreciate that the cutter tip 22 may also have multiple threads, a discontinuous thread or no threads. For example, a series of radially outwardly extending blades or posts arranged in a helical pattern around the tubular body can be provided. As shown in FIG. 3, the distal portion of the thread 46 advantageously has its leading edge rounded or broken to remove the sharp corner. By eliminating the sharp edge, the risk of accidental damage to the patient is reduced. The distal edge of the cylindrical body 30 and cutter blocks 42 may also be chamfered to eliminate sharp edges.

One embodiment of the cutter tip 22 is rotatably retained in a first embodiment of a cutter housing 21. The illustrated housing 21 is externally a double step cylinder having a proximal end 50 and a distal end 52 as shown in FIG. 2. The distal exterior diameter is approximately 0.0790 inches; however, the distal exterior diameter may range from about 0.039 to about 0.150 depending upon cutter tip design and the intended clinical application. The distal section 53 in the illustrated embodiment is about 0.117 inches in length but the length may vary from about 0.020 to about 0.50. The outside diameter of the proximal section may be less than the diameter of the distal section to produce an annular shoulder 51 to limit concentric proximal advance of the proximal section within the tubular body 12. The proximal section extends axially for approximately 0.09 inches but it may vary as will be understood by those of skill in the art.

In general, the cutter housing 21 may be secured to the distal end of the tubular body 12 in accordance with any of a variety of techniques which will be known to those of skill in the art. The concentric overlapping joint illustrated in FIG. 2 can be utilized with any of a variety of secondary retention techniques, such as soldering, the use of adhesives, solvent or thermal bonding. Alternatively, or in conjunction with any of the foregoing, an outer tubular sleeve may be heat shrunk over the joint between the cutter housing 21 and the tubular body 12.

The interior configuration of the present cutter housing 21 is principally a stepped cylinder as shown in FIG. 2. The distal internal diameter is approximately 0.0689 inches and may range from about 0.050 to about 0.150. The proximal end of the present cutter housing has an internal diameter of approximately 0.0558. The internal diameter can alternatively range from about 0.035 to about 0.130.

At the proximal end of the distal step is a shallow radially outwardly extending retaining groove 54. The retaining groove 54 is approximately 0.0015 deep relative to the distal section and may range in depth from about 0.0005 to about 0.020. The retaining groove 54 in the illustrated embodiment is about 0.0135 in axial width; however, as one skilled in the art will readily appreciate, the groove width may be varied and still accomplish its retention function.

As illustrated in FIG. 2, the retaining groove 54 cooperates with the cutter blocks 42 of the present cutter tip 22 to retain the cutter tip 22 within the cutter housing 21. The cutter blocks 42 provide a bearing surface for the cutter tip 22 to facilitate the rotational movement. In addition, due to the cooperative engagement between the cutter blocks 42 and the retaining groove 54, the cutter tip 22 is substantially restrained from axial movement within the cutter housing 21.

As shown in FIG. 2, the distal end 36 of the illustrated cutter tip 22 is approximately axially aligned with the distal end 52 of the cutter housing 21. As such, the length of the cutter housing 21 distal of the retaining groove 54 corresponds to the length of the cutter tip 22 which extends distally from connector 40. By creating a substantially flush surface at the distal end 52 of the cutter housing 21 and cutter tip 22, the possibility of accidental damage to the intima from the cutter tip 22 is reduced. One skilled in the art will readily recognize, however, that the distal end 36 of the cutter tip 22 may alternatively extend beyond, or be recessed within, the distal end 52 of the cutter housing 21.

Figure 5B:
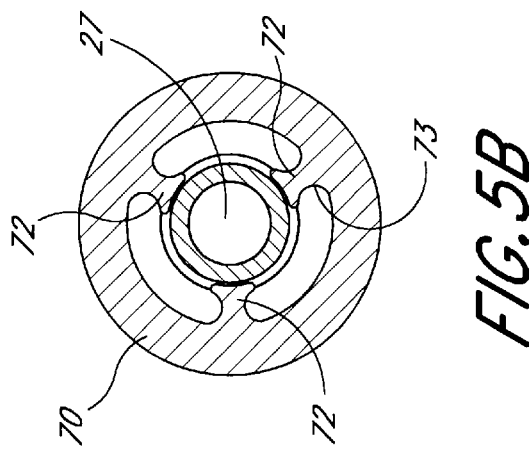
FIG. 5B is a cross-sectional view of the cutter tip and housing taken along the lines 5B—5B of FIG. 5A.
Figure 5A:
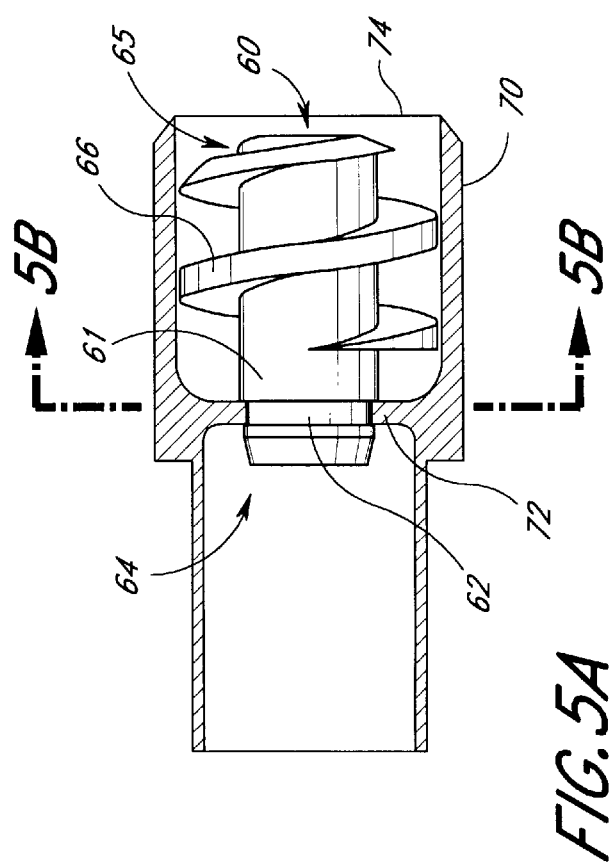
FIG. 5A is a cross-sectional side elevational view of a second embodiment of the cutter tip and housing.

A second embodiment of the cutter tip 60 and associated cutter housing 70 are illustrated in FIGS. 5A and 5B. The second embodiment of the cutter tip 60 is principally a radially symmetrical structure such as a cylindrical body 61 having an annular retention structure such as a retaining groove 62 located near the proximal end 64. The retaining groove 62 in the illustrated embodiment is about 0.007 deep, and about 0.008 wide, although both can be varied as may be desired. Proximal to the retaining groove 62, the outside diameter of the cylindrical body tapers from about 0.04 to about 0.036. Preferably, all edges are broken or chamfered to ensure burr free corners and facilitate assembly. The second embodiment of the cutter tip 60 also has a generally helical thread 66 similar to that of the first embodiment.

The second embodiment of the cutter tip 60 is snap fit within a second embodiment of the cutter housing 70. The second embodiment of the cutter housing 70 is similar to the first embodiment with the exception that the retaining groove of the first housing is replaced by a set of radially inwardly extending retaining members 72. As shown in FIG. 5B, the present cutter housing 70 has three retaining members 72, preferably circumferentially symmetrically distributed (i.e. on 120° centers). One skilled in the art will recognize that the number, size and shape of the retaining members can vary. At least two will generally be used to achieve opposition, and embodiments having 3, 4, 5 or more may be readily produced.

The retaining members 72 serve the added function of stationary cutter blocks in the second embodiment. As such the retaining members 72 should be sized accordingly. The illustrated retaining members 72 are about 0.007 inches thick in the axial direction; however, one skilled in the art will appreciate that the thickness can range from about 0.003 to about 0.030 or otherwise depending upon material choice and the desired degree of axial restraint. The retaining members 72 extend about 0.007 inches inward from the interior wall of the cylindrical cutter housing 70. The retaining member 72 length can vary, however, depending upon the desired dimensions of the cutter housing and tip body. As shown in FIG. 5B, the side edges 73 of the retaining members 72 may be provided with a radius such that the radial interior and exterior ends are wider than the central portion.

As one skilled in the art will appreciate, the retaining members 72 are provided to engage within the retaining groove 62 of the cutter tip 60 such that the cutter tip 60 is substantially restrained from axial movement relative to the cutter housing 70. The retaining members 72 also provide a bearing surface for the rotational movement of the cutter tip 60 relative to the cutter housing 70. Similar to the first embodiment, the distal end 65 of the cutter tip 60 is approximately flush with the distal end 74 of the cutter housing 70. Alternatively, the distal end 65 of the cutter tip 60 can be slightly recessed within the distal end 74 of the cutter housing 70 by as much or more than is shown in FIG. 5A.

As indicated in FIG. 2, the distal end of a flexible drive 24 is firmly secured within the axial bore 27 of the cutter tip 22. The cutter tip 22 is secured to the flexible drive 24 by any of a variety of ways such as crimping, soldering, interference fit structures, and/or threaded engagement as will be apparent to those of skill in the art. Alternatively, the flexible drive 24 could extend axially through the cutter tip 22 and be secured at the distal end 36 of the cutter tip.

The flexible drive 24 is preferably a hollow, laminated flexible "torque tube" such as may be fabricated from an inner thin-wall polymeric tubing, an intermediate layer of braided or woven wire, and an outer polymeric layer. In one embodiment, the torque tube comprises a polyimide tube having a wall thickness of about 0.004 inches, with a layer of braided 0.0015 inch stainless steel wire embedded therein.

The laminated construction produces a tube with a very high torsional stiffness and surprising tensile strength, but which is reasonably flexible with respect to the longitudinal axis. However, depending upon the desired torque transmission, diameter and flexibility, any of a variety of other materials and constructions can also be used. In general, the drive tube must have sufficient torsional rigidity to drive the cutter tip through reasonably foreseeable blockages.

The outside diameter of one embodiment of the present hollow flexible drive tube is approximately 0.032 inches, but can range between about 0.020 inches and about 0.034 inches or more. One skilled in the art will appreciate that the diameter of the flexible drive tube 24 is limited by the minimum torsional strength and guidewire diameter at the low end, and maximum permissible catheter outside diameter at the high end.

The selection of a hollow drive tube allows the device to be advanced over a conventional spring-tipped guidewire, and preferably still leaves room for saline solution, drugs or contrast media to flow through the lumen of the drive tube and out of the distal opening on the cutter tip. The internal diameter of the present hollow flexible drive tube is thus partially dependent upon the diameter of the guidewire 28 over which the flexible drive tube 24 must track. The internal diameter of the guidewire lumen in one embodiment of the present hollow flexible drive tube intended for use with a 0.018 inch diameter guidewire, for example, is approximately 0.024 inches. Because the flexible drive tube 24 extends between the control 18 and the cutter tip 22, the length of the present hollow flexible drive tube 24 must be sufficient to allow the cutter assembly to reach the target occlusion while also allowing adequate space outside of the patient for the operator to manipulate the instrument.

The lumen 20 of the assembled device is thus an annular space defined between the inside wall of the flexible tubular body 12 and the outside of the flexible drive tube 24. This lumen 20 is used to aspirate fluid and material from the cutter. Preferably, sufficient clearance is maintained between the tubular body 12 and the rotating drive tube 24 to minimize the likelihood of binding or clogging by material aspirated from the treatment site.

In general, the cross-sectional area of the lumen 20 is preferably maximized as a percentage of the outside diameter of the tubular body 12. This permits an optimization of maintaining a minimal outside diameter for tubular body 12, while at the same time permitting an acceptable flow rate of material through the aspiration lumen 20, with minimal likelihood of clogging or binding which would interrupt the procedure. Cross-sectional area of the aspiration lumen 20 is thus optimized, if the drive tube is constructed to have relatively high torque transmission per unit wall thickness such as in the constructions described below. In one embodiment of the invention, intended for coronary artery applications, the outside diameter of tubular body 12 is about 0.080. The wall thickness of tubular body 12 is about 0.008, and the outside diameter of torque tube 24 is about 0.031. This produces a cross-sectional area of the available portion of central lumen 20 of about 0.00245 square inches. This is 50% of the total cross-sectional area of the tubular body 12. Preferably, the cross-sectional area of the lumen 20 is at least about 25%, more preferably at least about 40%, and optimally at least about 60% of the total cross-sectional area of the tubular body 12.

The tubular body 12 may comprise any of a variety of constructions, such as a multilayer torque tube. Alternatively, any of a variety of conventional catheter shaft materials such as stainless steel, or single layer polymeric extrusions of polyethylenes, polyethylene terephthalate, nylon and others well known in the art can be used.

In one embodiment, for example, the tubular body 12 is a PEBAX extrusion having an outside diameter of approximately 0.090 inches. However, the outer diameter can vary between about 0.056 for coronary vascular applications and about 0.150 for peripheral vascular applications. Also, because the tubular body 12 must resist collapse under reasonably anticipated vacuum forces, the foregoing tubular body 12 has a wall thickness of at least about 0.005 inches. The wall thickness can, however, be varied depending upon materials and design.

The distal end of the tubular body 12 is affixed to the proximal end 50 of the cutter housing 22 as shown in FIG. 2. The proximal end of the tubular body 12 is affixed to the control 18 as described below.

Figure 6:
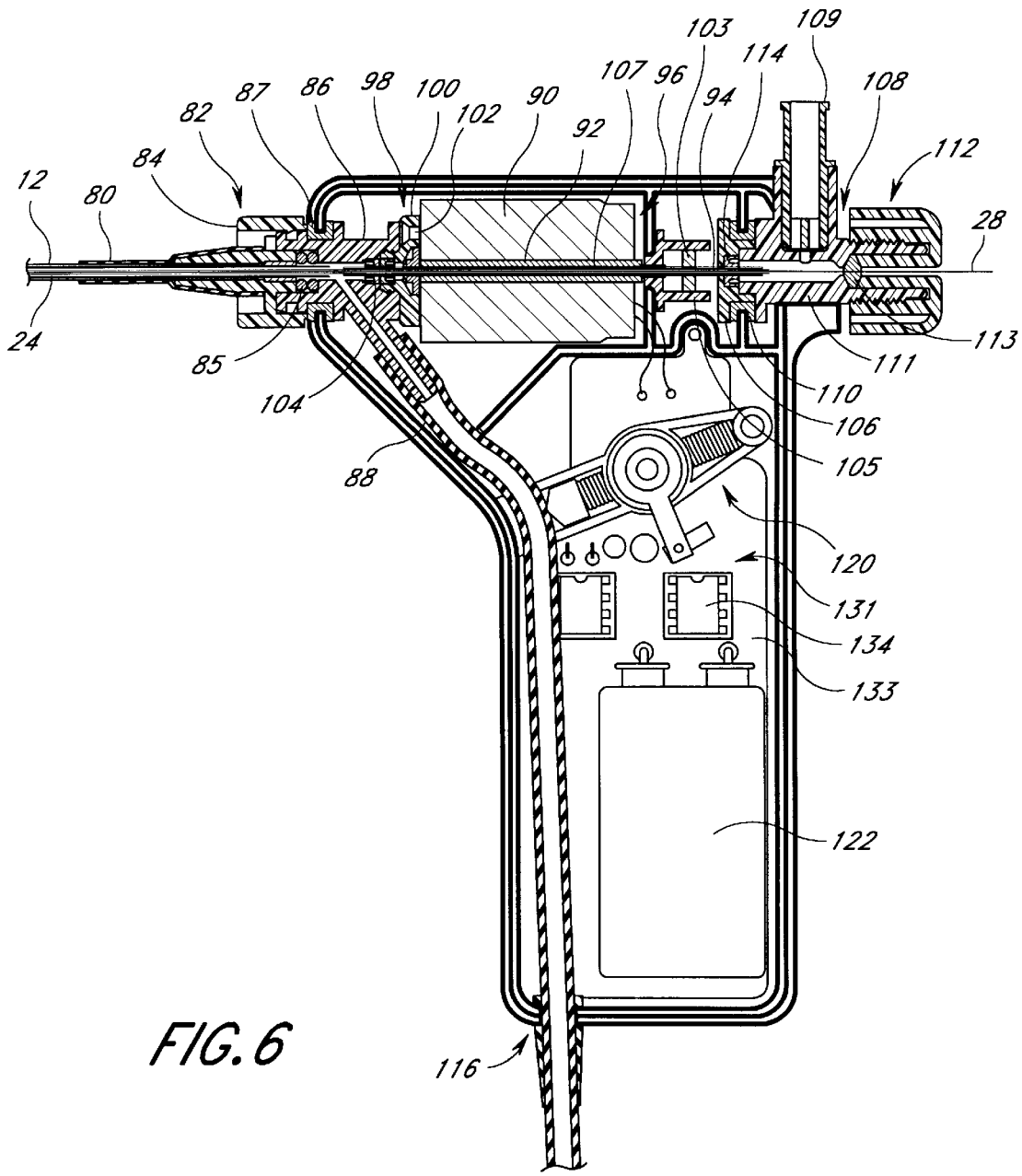
FIG. 6 is a side elevational cross-section of a control in accordance with one embodiment of the invention.

A reinforcing tube 80 extends from the control 18 unit along a proximal portion of the tubular body 12. The reinforcing tube provides support to avoid over bending and kinking at the proximal end of the drive tube 24. The point at which the flexible drive tube 24 is rigidly connected to the control 18 is a likely point of damaging bending forces. As such, the reinforcing tube 80 is provided to reduce the likelihood of a failure at that location due to bending forces. The reinforcing tube 80 extends distally over the tubular body 12 at least about 3 cm and preferably about 6 cm, and comprises silicone or other conventional biocompatible polymeric material. As shown in FIG. 6, the reinforcing tube 80 is fastened to the control 18 such as by interference fit over a snap tip assembly 82 through which the flexible drive tube 24 and tubular body 12 enter the control 18. Thus, the reinforcing tube 80 envelopes a proximal portion of the tubular body 12.

The flexible drive tube 24 and tubular body 12 operatively connect the cutter tip 22 and cutter housing 21 to the control 18. The tubular body 12 and drive tube 24 enter the control 18 through the snap tip assembly 82 as shown FIG. 6. The snap tip assembly 82 is provided with a connector such as a hub 84 having a central lumen in communication with a vacuum manifold 86. The tubular body 12 is connected to the hub 84. The hub 84 is rotatable, and enables the user to rotate the tubular body 12 relative to the control 18.

The tubular body 12 may be reinforced internally where it passes through the hub 84 by a thin-wall stainless steel tube (not shown) that extends through and is bonded to the hub 84. Since it is difficult to bond to acetal, in the case of a white acetal (Delrin) hub, for example, a portion of the injection-molded hub 84 bore can be hexagonal or other non circular cross-sectional shape. Epoxy adhesive (not shown) injected into this space around the stainless steel tube acts like a spline, preventing the tube from rotating in the hub or pulling back out.

The acetal hub 84 bonded to the proximal end of the tubular body 12 provides a means of rotating the snap tip assembly 82 relative to the control 18. Friction to limit this rotation is provided by the face of a grommet 87 compressed against the proximal perimeter flange of the hub. Acetal (Delrin) may be used for the hub 84 to provide long-term memory of the snap-fit tabs that secure this part to the rest of the assembly. The hub 84 snaps onto and seals with the vacuum manifold 86.

As best seen in FIG. 6, an injection molded acrylic vacuum manifold 86 is fastened to a vacuum hose 88 at one outlet and to a motor 90 at a second outlet. The hub-end of the vacuum manifold 86 houses two silicone rubber O-rings 85 that function as dynamic (rotatable) seals between the manifold walls and the tube. The opposite end of the manifold, where the proximal end of the drive tube 24 is visible, contains a pair of butyl rubber fluid seals 104. The two vacuum manifold fluid seals 104 are mounted back-to-back, with the lips pointing away from each other. In this configuration, the innermost seal protects against positive pressure leaks such as blood pressure and the outer-facing seal excludes air when the system is evacuated. These dynamic seals may be lubricated with silicone grease.

The vacuum manifold 86 is connected to a motor 90 through use of a threaded motor face plate 100. The vacuum manifold 86 is threaded onto the face plate 100. The face plate 100 is attached to the output end of the motor 90 by a threaded fastener 102. The present motor 90 is a modified 6-volt D.C. hollow-shaft, 22 mm O.D. motor built by MicroMo, regulating both speed and torque as required as discussed below.

Power is transmitted from the motor 90 to the drive tube 24 by adhesive bonding a length of medium-wall stainless steel tubing, such as hypodermic needle stock measuring 0.036" I.D.×0.053" O.D. before coating, around the driven proximal end of the drive tube 24. This rigid tube, called the drive shaft, is a concentric slip fit through the 0.058" I.D. of the hollow motor shaft, and extends beyond the length of the motor shaft in both directions. The drive shaft is coated on the outer surface with 0.001" of Type-S Teflon. The Teflon-coated, exposed ends of the drive shaft provide a smooth wear-surface for the dynamic fluid seals.

A small drive plate 103, bonded to the rear end of the drive shaft 107, mates with a drive sleeve 105 permanently attached to the 0.078" O.D. motor shaft 92. Together, the drive plate 103 and sleeve 105 form a concentric drive coupling between the motor shaft 92 and the drive shaft 107, which in turn is bonded to the drive tube 24. The splined configuration of the drive coupler allows approximately ¼" of relative longitudinal movement between the plate 103 and sleeve 105, sufficient to accommodate thermal and mechanical changes in the relative lengths of the outer tube 12 and flexible drive tube 24. An integral flange on the drive sleeve 105 serves as a slinger to deflect fluid away from the rear motor bearings in the event of a leaking fluid seal.

The drive sleeve 105 and drive plate 103 are preferably molded from Plexiglas-DR, a medical-grade, toughened acrylic resin made by Rohm and Haas. These parts have shown little tendency to crack in the presence of the chemicals that might be present or used in the assembly of the device; these chemicals include cyanoacrylate adhesives and accelerators, motor bearing lubricants, alcohol, epoxies, etc. The drive sleeve 105 and drive plate 103 are lightly press-fitted to their respective shafts 92, 107, and secured with a fillet of adhesive applied to the outside of the joints.

To the right of the motor 90 in FIG. 6 is an infusion manifold 108. This is designed exclusively as an input circuit; theoretically any fluid that can be pumped or injected at a pressure exceeding the diastolic pressure in the artery or vein could be used, but saline solutions, therapeutic drugs and fluoroscope contrast media are the ones most likely to be used with this device. Saline solutions are needed to purge air from the tubular body 12 before the procedure to prevent air embolism, and may also be used during the atherectomy procedure to provide a continuous flow of liquid (other than blood) during cutting to help carry debris through a return circuit. In this case, an elevated I.V. bag may be used to ensure a continuous, low-pressure flow through the system.

At various times during the procedure, the surgeon may request that a bolus of contrast medium be injected to enhance the fluoroscopic image of the artery or vein, either to position or direct the guide wire, locate the blockage, or to confirm that the stenosis has indeed been reduced. Contrast medium is a relatively dense material and high pressure (several atmosphere) is usually required to force the material quickly through a small, elongated lumen 26 of the drive tube 24.

In the case of the present surgical instrument, the infusion manifold 108 is comprised of several components. The first component is an infusion port which may contain a medical infusion valve 109 such as that supplied by Halkey-Roberts Corp. This silicone rubber check valve assembly is designed to be opened by insertion of a male Luer-taper (or lock) fitting. The valve stays open as long as the taper fitting remains in place, but closes immediately if it is withdrawn. This action provides simple access when needed, but provides the required backflow prevention to minimize loss of blood through this route. The infusion valve 109 is permanently bonded into the side arm of the flush port manifold 111, an injection-molded, transparent acrylic fitting.

The flush port manifold 111 has an integral threaded extension that protrudes from the right-hand side of the control 18. The threaded extension is provided with a silicone guide wire seal 113, and an acetal (Delrin) guide wire clamp nut 112 that together function as a hemostasis valve compression-fitting. The guide wire 28 extends through both the seal and the nut 112.

With the clamp nut 112 screwed in or tightened, the silicone guide wire seal 113 compresses against the guide wire 28, locking it in place, and preventing leakage of blood or air. When it is necessary to slide the guide wire 28 or to slide the surgical instrument 10 along the guide wire 28, the clamp nut 112 must be loosened to reduce the clamping action somewhat. If no guide wire 28 is used, the seal 113 compresses against itself and closes off the passageways to leakage. Delrin may be used for the clamp nut 112 to minimize stiction and galling of the threads during use. An internal shoulder on the threaded portion of the nut acts as a position stop, preventing extrusion of the seal 113 that might otherwise result from over-tightening.

A fluid channel extends up the center of the flush port manifold 111, continuing through the open lumen of the drive tube 24, all the way out through a distal aperture 39 in the tip of the helical cutter tip 22. The guide wire 28 follows the same path. A leak-proof between the flush port manifold 111 and the drive tube 24 is desirable. Accordingly, a molded acrylic flush port flange 106 is bonded to the motor end of the flush port manifold 111, creating a chamber housing a low durometer butyl rubber lip seal 114. The tiny rubber part forms an effective dynamic seal against one end of the Teflon-coated drive shaft 107 bonded around the end of the drive tube 24. Lip seals are pressure-compensating devices that function at zero or low pressure by light elastomeric compression against a shaft, minimizing the drag component in a dynamic application. When pressure against the seal increases, the lip tightens against the shaft, increasing both the sealing action and the dynamic friction. In this application, however, a high pressure sealing requirement only occurs during injection of contrast medium, typically when the cutter tip 22 is stopped. Lower pressure dynamic sealing is required during saline infusion, however, so pressure compensating lip seals are an ideal design solution here. Lip seals are inherently directional devices, sealing in one direction, and pressure-relieving in the other. Care must be taken to position the fluid seals properly in each application.

The fluid seal 104 is transfer-molded butyl rubber, with a 0.047" (generally within the range of from about 0.035 to about 0.050 inches) lip I.D., running on a silicone-grease-lubricated, Teflon-coated drive shaft 107 with a 0.055" O.D. The medical-grade silicone grease reduces friction quite well, but tends to be forced away from the lip during prolonged use. The Teflon coating on the drive shaft acts as a back-up lubricant that prevents seal damage in the event the grease is lost. Frictional drag is acceptably low with this arrangement, yet sealing appears adequate to prevent leakage during use.

Moving back to the Y-shaped coupling unit 86, a heavy walled silicone rubber vacuum hose 88 is attached to the remaining port of the Y-shaped vacuum manifold 86. The vacuum hose 88 generally extends between the Y-shaped coupler 86 of the control 18 and a vacuum source 19 such as the house vacuum of the catheter lab of a hospital or a vacuum bottle.

The vacuum hose 88 extends down through a pinch valve switch configuration 120 described in detail below. The vacuum hose 88 then further extends to the bottom portion of the control 18. A pinch resistant sleeve 116 is preferably provided to prevent the pinching of the vacuum hose 88 as it exits the control 18. Additionally, the pinch resistant sleeve 116 provides a liquid seal to prevent liquids from entering the control 18 unit during operation.

Figure 7A:
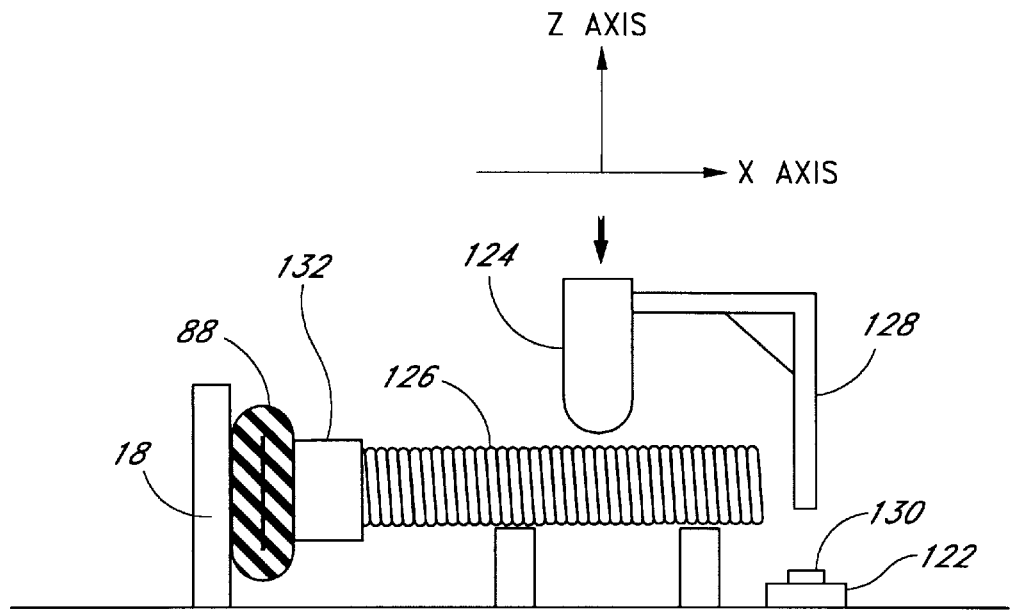
FIG. 7A is a schematic illustration of a pinch-valve switch in a closed position.
Figure 7B:
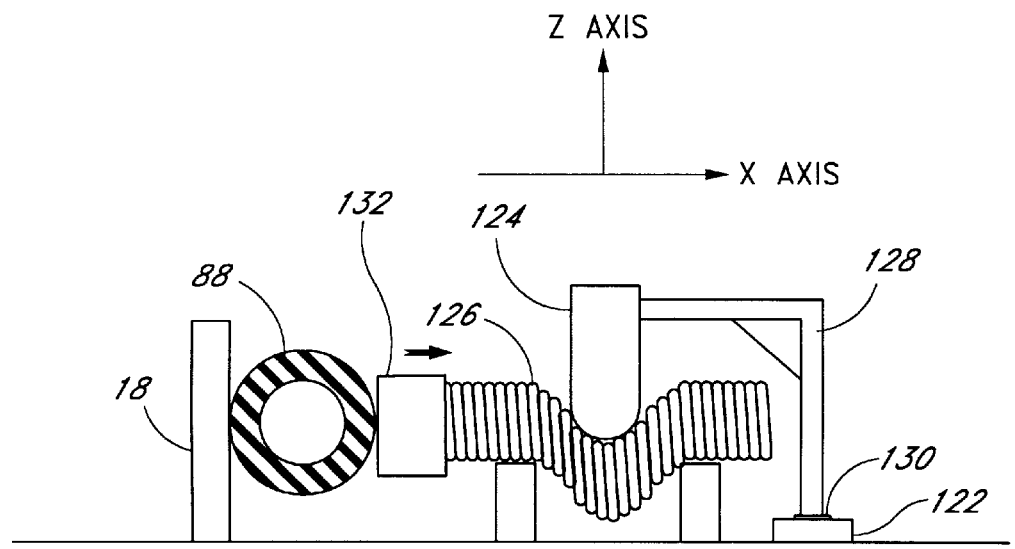
FIG. 7B is a schematic illustration of a pinch-valve switch in an open position.

Returning to the pinch valve switch configuration 120, the pinch valve switch 120 provides a means to assure that the motor 90 driving the rotatable drive shaft 24, which in turn drives the cutter tip 22, is not activated unless the vacuum is being applied. As such, power from the power source 122 is provided to the motor through an electronic switch 130. The pinch valve switch 120 comprises a push button oriented along the Z axis shown in FIG. 7A. The switch push button 124 can translate along the Z axis when depressed by the user. The lower portion of the push button is provided with a unshaped cut out forming a tunnel along the x-axis. The cut out is sized to correspond to a compression spring 126. The present compression spring 126 is a precision-length stack-wound button spring fabricated from 0.027" diameter 302 stainless steel wire, with a closed retainer loop at one end. The push button 125 is located along a portion of the compression spring 126 such that the push button 124 rests on the compression spring 126 and is supported in an up position. The switch push button 124 thus can travel to a down position when pressed by the operator as shown in FIG. 7B. The compression spring 126 provides a bias such that the push button 124 will return to the up position when released.

The switch push button 124 is further provided with an axial arm 128 which extends in a direction perpendicular to the direction of travel of the push button 124. The electronic switch 130 is located below the axial arm 128 of the switch push button 124. As the switch push button 124 is depressed, contact is made on the electrical switch 130. The electrical switch 130 allows current to flow from a power source 122 to the motor. Thus, depression of the push button 124 creates a flow of current which drives the motor 90. The motor drives the drive tube 24 and cutter tip 22 of the present surgical instrument 10.

Advantageously, the compression spring 126 is attached to a pinching member 132 of a pinch valve. As the push button 124 is depressed, the compression spring 126 is deflected. The deflection in the compression spring 126 causes the pinch member 132 to retract. Thus, the pinch member 132 is retracted as soon as the push button 124 depression begins. As the pinch member 132 is retracted, a vacuum flow is allow to pass through the pinch valve 120. Advantageously, the amount of flow through the valve depends on how far the button 124 is depressed, making it easy to control the amount of suction. Depressing the button further to the switch contact makes the vacuum open fully. Thus, depressing the button starts the vacuum first and then cutting action is started second to eliminate the risk of cutting without aspiration. Because repeated cycles of opening and closing the valve tend to shift the position of the tube, internal ribs are preferably provided in the control 18 to hold the tube in the right place.

The return flow path in the lumen 20 of the outer tube 12 outside the drive tube 24, augmented by suction from an external vacuum source, starts at the cutter tip 22, spirals through the helical thread 46 and the cutter blocks 42 of the cutter tip 22, through the outer lumen 20 of the outer tube 12 to the vacuum manifold 86, and then through a length of vacuum tubing 88 to a tissue collection/fluid separation container suspended from the I.V. Pole. The collection container is connected to a vacuum collection canister that may be, in turn, hooked to a regulated central vacuum source or a suction collection pump or vacuum container. Flow through the vacuum manifold 86 is controlled by the pinch valve mechanism 120 integral to the drive module; this is actuated by the same spring-loaded button that starts the drive motor. The current is not allowed to flow to the motor 90 until the push button 124 completes its travel. Thus, the depression of the push button 124 controls the vacuum such that the motor 90 is not energized without the vacuum first flowing.

The pinch valve assembly is preferably designed with a "lock-out" feature (not shown) that secures the button 124 in a partially depressed position where the vacuum tube 88 is no longer compressed, but the switch 130 is not yet actuated. This preserves the elastic memory of the pinch tube and protects the device from accidental actuation during handling or storage. In its present form, a thin, flexible lock-out wire with an identifying tag (not shown) can be inserted at the last stage of assembly, passing through a hole in the button (not shown) and extending through a notch in the sidewall of the control 18. In this configuration, the highly-visible tag protrudes from the side of the control 18, preventing use of the device until the wire is pulled free. This action releases the button 124 and returns the control 18 to a functional condition. Once removed from the original locked position, the lock-out wire (not shown) cannot be reinserted without disassembly of the control 18.

The motor and feedback indicators of the device 10 are controlled by electronic circuitry 131 such as may be contained on a printed circuit board 133. The circuitry providing the power to the motor 90 also provides a means for checking the load on the motor. As known to those skilled in the art, when a D.C. motor as used in this invention encounters resistance to rotational movement, an increased load is placed on the power source 122. Accordingly, the circuitry 131 is provided with the capability to identify and indicate the speed and/or torque.

In one embodiment, a motor controller 134 provides the motor 90 with the required energy by using a combination of missing pulse and pulse width modulation. The motor speed is sensed by measuring the back electromotive force (EMF), which is proportional to speed. A portion of the back EMF is fed to the controller 134, which varies the drive power to the motor 90 to maintain a constant speed. The circuit values of the controller 134 allow speed settings of 1,000 to 8,000 RPM. The speed chosen for no load operation in one embodiment is 3,200 RPM. Motor torque is limited to from about 0.10 to about 0.45 oz-inches by sensing the motor current and reducing the motor drive power to the appropriate level.

The power source 122, preferably a 9-volt battery, is not connected to the controller 134 until the push button 124 is depressed, so there is no standby power drain. In the illustrated embodiment, a green light emitting diode (LED) is on when the motor is running at normal loads. A red LED turns on at a motor current of approximately 0.25 amperes, indicating "overload." A switching controller is used for two reasons: (a) it is very efficient—it uses less than 0.015 amperes (the motor current would vary from 0.05 to 0.4 amperes, or perhaps more), and (b) it can deliver maximum torque instantly or demand, even at low motor speeds, so the likelihood of stalling is minimized.

Alternatively, any of a variety of tactile, auditory or visual alarms can be provided. For instance, the surgical instrument could vibrate or provide an audible signal when it encounters an overload situation. The pulses or tones may vary to correspond to any variance in resistance to rotation. For example, the pitch may increase with resistance or the speed of a repeating pulse of sound may increase. Additionally, where a (CRT) monitor is used to visualize the operation, a visual signal could be sent to the monitor to display the operating characteristics of the surgical equipment. As will be further recognized to those skilled in the art, other variations of alerting the operator to the operating characteristics of the present invention may be provided.

The present invention thus provides feedback to the clinician in real time during the progress of the rotational atherectomy procedure. Real time feedback can allow the clinician to adjust the procedure in response to circumstances which may vary from lesion to lesion, thereby enhancing the overall efficiency of the procedure and possibly minimizing additional risks such as the creation of emboli. Pressing the cutter tip 22 into a lesion with too much force will produce an increased load, which can then be detected by the circuitry 131 and communicated to the clinician in any of a variety of ways as has been discussed. This will allow the clinician to ease back on the distal advancement force and/or adjust the vacuum or RPM of the cutter tip 22 until the load is reduced to an acceptable level, and continue with the procedure.

In addition, increased load can be incurred by kinking along the length of the catheter shaft, thereby reducing the motor speed. Kinking originated loading will be reflected in the feedback mechanism to the clinician, so that the clinician can assess what corrective action to take.

In use, a guidewire 28 is first percutaneously introduced and transluminally advanced in accordance with well known techniques to the obstruction to be cleared. The surgical instrument 10 is then introduced by placing the cutter tip 22 on the guidewire 28, and advancing the cutter tip along the guidewire 28 through the vessel to the treatment site. When the cutter tip 22 has been maneuvered into the correct position adjacent the proximal terminus of material to be removed, the drive tube is rotated relative to the tubular body 12 to cause the cutter tip 22 to rotate in a direction which will cause the forward end of the thread 46 to draw material into the housing 21. A circular cutting action is provided by mutual cooperation of the outer cutting edge of the screw thread 46 with the sleeve of the cutter housing 21 and the internal peripheral wall of the cutter housing 21. In addition, the cutter housing 21 in cooperation with the cutter blocks 42, effectively breaks the strands of material being drawn into the cutter housing 21. The cut material is then carried proximally through the annular passageway between the flexible drive tube 24 and the tubular body 12 under the force of vacuum. If an increase in load and/or decrease in RPM is defected, the clinician can take reactive measures as described above. The vacuum then pulls the cuttings through the entire length of the lumen 20 and vacuum tube 88 and into a suitable disposal receptacle. The vacuum source may be regulated by a manual or automatic regulator such that a constant flow velocity may be maintained, or blockages reduced or cleared, through the vacuum tube 88 regardless of the viscosity of the material passing through the vacuum tube 88.

Although this invention has been described in terms of certain preferred embodiments, other embodiments apparent to those of ordinary skill in the art are also within the scope of this invention. Accordingly, the scope of this invention is intended to be defined only by the claims that follow.

What is claimed is:

1. A rotational medical device comprising:

an elongate flexible tubular body, having a proximal end and a distal end;

a rotatable element extending through the body;

a rotatable tip at the distal end of the body and connected to the rotatable element;

a control on the proximal end of the body;

an indicator in electrical communication with the control, for indicating resistance to rotation of either the rotatable element or rotatable tip; and an annular space between the rotatable tip and an interior wall of the tubular body.

2. A rotational medical device as in claim 1, wherein the indicator comprises a source of tactile feedback.

3. A rotational medical device as in claim 1, wherein the indicator comprises at least one light.

4. A rotational medical device as in claim 1, wherein the rotatable tip comprises a generally helical flange.

5. A rotational medical device as in claim 1, wherein the rotational tip is positioned inside of the tubular body.

6. A rotational medical device as in claim 1, wherein the rotatable tip is spaced radially inwardly from the interior wall of the tubular body by a distance within the range of from about 0.0001 to about 0.008 inches.

7. A rotational medical device as in claim 1, further comprising a thread on the rotatable tip.

8. A rotational medical device as in claim 7, wherein the thread extends between about 0.25 turns and about 10 turns around the rotatable tip.

9. A rotational medical device as in claim 8, wherein the thread is discontinuous.

10. A rotational medical device as in claim 7, wherein the rotatable tip has an axial length within the range of from about 0.040 inches to about 0.120 inches.

11. A rotational medical device as in claim 7, wherein the thread comprises a pitch within the range of from about 0.005 to about 0.060.

12. A rotational medical device as in claim 7, wherein the distal end of the rotatable tip is approximately axially aligned with the distal end of the tubular body.

13. A rotational medical device as in claim 7, wherein the distal end of the rotatable tip extends beyond the distal end of the tubular body.

14. A rotational medical device as in claim 7, wherein the rotatable tip is recessed within the tubular body.

15. A rotational medical device as in claim 1, further comprising at least two radially outwardly extending cutter blocks on the rotatable tip.

16. A rotational medical device as in claim 15, further comprising an annular retaining groove in the tubular body, for receiving the cutter blocks.

17. A rotational medical device as in claim 1, wherein the rotatable element comprises a torque tube.

18. A rotational medical device as in claim 17, wherein the torque tube comprises a layer of braided wire.

19. A rotational medical device as in claim 17, comprising a central guidewire lumen extending throughout the length of the rotational medical device.

20. A rotational medical device as in claim 1, wherein the rotatable tip further comprises a radially inwardly extending annular recess.

21. A rotational medical device as in claim 20, wherein the tubular body further comprises a plurality of radially inwardly extending retaining members for rotatably engaging the annular recess.

22. A method of removing material from a vessel, comprising the steps of:

providing an elongate, flexible, tubular body, having a proximal end and a distal end, a rotatable tip at the distal end of the tubular body, and a control on the proximal end of the tubular body;

advancing the distal end of the tubular body transluminally to the material;

rotating the rotatable tip;

drawing portions of the material proximally past the rotatable tip and into the tubular body; and providing feedback to the operator in response to changes in the load on the rotatable tip.

23. A method as in claim 22, wherein the drawing step is accomplished by connecting a vacuum source to the proximal end of the tubular body.

24. A method as in claim 23, wherein the advancing step comprises advancing the tubular body along a guidewire.

25. A method as in claim 23, wherein the advancing step comprises advancing the tubular body through a percutaneous access device.

26. A method as in claim 23, further comprising the step of infusing fluid through a flush port on the proximal end of the tubular body.

27. A method as in claim 22, wherein the advancing step is accomplished by applying axial distal pressure on the tubular body, and further comprising the step of reducing the amount of axial distal pressure in response to feedback indicating a change in the load on the rotatable tip.

28. A method as in claim 23, wherein the control both activates the vacuum and commences rotation of the rotatable tip.

29. A method of removing material from a patient comprising:

providing an elongate flexible tubular body, having a proximal end and a distal end, a rotatable tip on the distal end of the tubular body, and a control on the proximal end of the tubular body;

advancing the distal tip of the tubular body to the material to be removed;

manipulating the control to activate a vacuum through the tubular body; and manipulating the control to commence rotation of the rotatable tip to remove material from the patient; and infusing fluid through a guidewire flush port on the proximal control.

30. A rotational medical device comprising:

an elongate flexible tubular body, having a proximal end and a distal end;

a rotatable element extending through the body;

a rotatable tip at the distal end of the body and connected to the rotatable element;

a control on the proximal end of the body;

a guidewire lumen extending through the rotatable element; and an axially extending aspiration channel between the rotatable element and the tubular body.

31. A rotational medical device comprising:

an elongate flexible tubular body, having a proximal end and a distal end;

a rotatable element extending through the body;

a rotatable tip at the distal end of the body and connected to the rotatable element;

a control on the proximal end of the body;

a guidewire lumen extending through the rotatable element;

the control being mounted on a handle configured for one hand operation of the rotational medical device, and the control capable of activating both rotation of the rotatable tip and application of the vacuum.

32. A rotational medical device as in claim 31, wherein the control is activateable by single finger operation, and, upon actuation thereof, initiates the application of vacuum within the tubular body before initiating rotation of the rotatable tip.

33. A rotational medical device as in claim 31, wherein the handle further comprises an infusion port, and a proximal guidewire port.

34. A method of removing material from a patient comprising:

providing an elongate flexible tubular body, having a proximal end and a distal end, a rotatable tip on the distal end of the tubular body, and a control on the proximal end of the tubular body;

advancing the distal tip of the tubular body to the material to be removed;

manipulating the control to activate a vacuum through the tubular body; and manipulating the control to commence rotation of the rotatable tip to remove material from the patient, wherein rotation of the tip can only be accomplished if the vacuum is on.

* * * * *